(12) United States Patent
Schalapski et al.

(10) Patent No.: US 8,394,998 B2
(45) Date of Patent: Mar. 12, 2013

(54) METHOD OF PRODUCING NEOPENTYL GLYCOL

(75) Inventors: Kurt Schalapski, Oberhausen (DE); Tonia Kretz, Darmstadt (DE); Thorsten Kreickmann, Oberhausen (DE); Peter Heymanns, Essen (DE); Rainer Lukas, Essen (DE); Rolf-Peter Schulz, Kriftel (DE)

(73) Assignee: Oxea GmbH, Oberhuasen (DE)

( * ) Notice: Subject to any disclaimer, the term of this patent is extended or adjusted under 35 U.S.C. 154(b) by 161 days.

(21) Appl. No.: 12/737,224

(22) PCT Filed: Jun. 12, 2009

(86) PCT No.: PCT/EP2009/004268
§ 371 (c)(1),
(2), (4) Date: Dec. 20, 2010

(87) PCT Pub. No.: WO2010/000382
PCT Pub. Date: Jan. 7, 2010

(65) Prior Publication Data
US 2011/0098515 A1    Apr. 28, 2011

(30) Foreign Application Priority Data
Jul. 2, 2008 (DE) .......................... 10 2008 031 338

(51) Int. Cl.
*C07C 31/20* (2006.01)
*C07C 27/26* (2006.01)
(52) U.S. Cl. ........................................ 568/853; 568/854
(58) Field of Classification Search .................. 568/799, 568/853, 854
See application file for complete search history.

(56) References Cited

U.S. PATENT DOCUMENTS 6,268,539 B1   7/2001  Sen-Huang et al. .......... 568/853
7,388,116 B2 * 6/2008  Maas et al. .................... 568/799

FOREIGN PATENT DOCUMENTS
WO      WO 99/35112        7/1999

* cited by examiner

*Primary Examiner* — Sikarl Witherspoon
(74) *Attorney, Agent, or Firm* — Michael W. Ferrell

(57) ABSTRACT

The present invention relates to a method of producing neopentyl glycol by addition of isobutyraldehyde and formaldehyde in the presence of a tertiary alkylamine as catalyst to give the hydroxypivalinaldehyde with subsequent liquid phase hydrogenation in the presence of a nickel catalyst at a temperature of 80 to 180° C. and at a pressure of 6 to 18 MPa in the presence of an aliphatic alcohol and in the presence of water.

20 Claims, No Drawings

METHOD OF PRODUCING NEOPENTYL GLYCOL

CLAIM FOR PRIORITY

This substitute specification is submitted as a national phase entry of International Patent Application No. PCT/EP2009/004268 filed on Jun. 12, 2009 (International Publication No. WO 2010/000382), entitled "Method of Producing Neopentyl Glycol" ("Verfahren Zur Herstellung von Neopentylglykol") which claims priority to German Patent Application No. DE 10 2008 031 338.6 filed on Jul. 2, 2008. The priorities of International Patent Application No. PCT/EP2009/004268 and German Patent Application No. DE 10 2008 031 338.6 are hereby claimed and the referenced priority applications are incorporated herein in their entireties.

BACKGROUND OF THE INVENTION

The present invention relates to a process for preparing neopentyl glycol by hydrogenating hydroxypivalaldehyde in the liquid phase over a nickel-containing catalyst in the presence of more than 15% by weight of water, based on the starting mixture.

Polyhydric alcohols or polyols possess considerable economic significance as a condensation component for forming polyesters or polyurethanes, synthetic resin coatings, lubricants and plasticizers. In this context, polyhydric alcohols of interest are particularly those which are obtained by a mixed aldol addition of formaldehyde with iso- or n-butyraldehyde. The aldol addition between formaldehyde and the appropriate butyraldehyde first forms an aldehydic intermediate which then has to be reduced to the polyhydric alcohol. An industrially important example of such a polyhydric alcohol obtainable by this process is neopentyl glycol [NPG, 2,2-dimethylpropane-1,3-diol], which is obtained by mixed aldolization of formaldehyde and isobutyraldehyde. The aldol addition reaction is performed with equimolar amounts in the presence of basic catalysts, for example, alkali metal hydroxides or aliphatic amines, and first affords the isolable hydroxypivalaldehyde (HPA) intermediate. This intermediate can subsequently be converted with excess formaldehyde in accordance with the Cannizzaro reaction to neopentyl glycol to form one equivalent of a formate salt. In this configuration of the reduction step, the formate salt is therefore obtained as a coproduct. However, also implemented industrially is the catalytic hydrogenation of hydroxypivalaldehyde in the gas and liquid phase over a metal catalyst. Suitable hydrogenation catalysts have been found, according to EP 0 278 106 A1 to be nickel catalysts which may comprise further active metals, such as chromium or copper, and additionally activators. The crude aldolization mixture is subsequently catalytically hydrogenated without preceding separation into its constituents or removal of individual components. Since formaldehyde is typically used as an aqueous solution, for example as a 37% by weight solution, water is present in the aldolization mixture to be hydrogenated. The crude hydrogenation product obtained can then be worked up by distillation according to the teaching of EP 0 278 106 A1.

A further process for hydrogenation of hydroxypivalaldehyde to neopentyl glycol in the liquid phase in the presence of nickel catalysts is known from WO 99/035112 A1. Particular reference is made to the harmful influence of too high an amount of water on the stability of the nickel catalyst during the hydrogenation process. There are reports of catalyst damage and also of a selectivity decline at the expense of neopentyl glycol as a result of the presence of water. WO 99/035112 A1 therefore proposes limiting the amount of water to less than 15% by weight in the hydrogenation of hydroxypivalaldehyde to neopentyl glycol. The hydrogenation temperature of 100° C. should also not be exceeded in the known processes, since the employment of higher hydrogenation temperatures in the presence of nickel catalysts results in enhanced by-product formation, such as the formation of neopentyl glycol monoisobutyrate or neopentyl glycol monohydroxypivalate.

WO 98/17614 A1 also considers the hydrogenation of hydroxy-pivalaldehyde to neopentyl glycol by the liquid phase process in the presence of nickel catalyst. In the known process, isobutyraldehyde is first reacted with an aqueous formaldehyde solution in the presence of a tertiary alkylamine to give a crude mixture comprising hydroxypivalaldehyde, which subsequently is subjected to an extraction with an aliphatic alcohol. The low-boiling components are distilled out of the organic phase, and the higher-boiling components which comprise hydroxypivalaldehyde are hydrogenated. For workup, the hydrogenation product is extracted with water, which transfers neopentyl glycol to the aqueous phase. Neopentyl glycol is then isolated from the aqueous phase by distillation. Extraction and distillation steps connected upstream of the hydrogenation stage reduce the amount of the water present in the hydrogenation stage. In the known processes, the hydrogenation stage should be performed within a temperature range from 120° C. to 180° C.

According to U.S. Pat. No. 6,268,539 B1 the aldolization product obtained from the reaction of isobutyraldehyde and an aqueous formaldehyde solution under triethylamine catalysis is first distilled. The resulting water-containing distillation residue is subsequently hydrogenated at 70 to 120° C. in the presence of Raney nickel which comprises molybdenum as a promoter. The known liquid phase process is characterized by the use of a specific self-aspirator agitator which ensures intensive mixing between the liquid and gaseous phases. As a result of this specific reactor configuration, only low hydrogenation pressures in the range from 0.55 to 12.4 MPa are required.

The reaction regime known from EP 0 395 681 B1 also allows the liquid phase hydrogenation of hydroxypivalaldehyde to be performed in the presence of Raney nickel using a specific reactor design in which hydrogen gas is passed intensively through the liquid reaction mixture. This stripping effect removes traces of the tertiary amine used as an aldolization catalyst and compounds thereof which promote the decomposition of the hydroxypivalaldehyde in the hydrogenation stage. According to the teaching of EP 0 395 681 B1, there is no need to employ high pressure. The crude mixture used in the hydrogenation stage contains 10 to 35% by weight of water.

For the liquid phase hydrogenation of hydroxypivalaldehyde to neopentyl glycol in the presence of nickel catalysts, either a special reactor design is required, or only low water contents in the crude hydroxypivalaldehyde are permitted for the use for hydrogenation, in order to convert hydroxypivalaldehyde at high conversion with high selectivity to neopentyl glycol. In some cases, the crude hydroxypivalaldehyde must first be subjected to an additional extraction and distillation in order to reduce the water content in the product to be hydrogenated.

It is, however, desirable to hydrogenate the reaction product from the alkylamine-catalyzed aldol addition of isobutyraldehyde with an aqueous formaldehyde solution directly and without purification steps in the presence of a common, industrially available nickel catalyst in the liquid phase.

It is therefore an object of the invention to develop a process which is simple to perform in technical terms and enables, with economically acceptable means, neopentyl glycol to be obtained by alkylamine-catalyzed aldol addition.

DETAILED DESCRIPTION OF THE INVENTION

The invention is described in detail below by reference to various examples and embodiments. Such discussion is for purposes of illustration only. Modifications to particular examples and embodiments within the spirit and scope of the present invention, set forth in the accompanying claims will be readily apparent to one of skill in the art.

Terminology used herein is given its ordinary meaning unless otherwise stated herein.

The invention therefore consists in a continuous process for preparing neopentyl glycol by addition of isobutyraldehyde and formaldehyde in the presence of a tertiary alkylamine as a catalyst to give hydroxypivalaldehyde with subsequent hydrogenation, characterized in that the hydrogenation is performed in a tubular reactor without internals and without stirrer apparatus and is effected at a temperature of 110 to 180° C. and at a pressure of 6 to 18 MPa in the presence of nickel catalysts in the homogeneous liquid phase which contains, as an organic solvent or diluent, an aliphatic alcohol in an amount of 15 to 27% by weight, based on the organic component in the starting mixture, and water in an amount of more than 15 to 25% by weight, based on the total amount used.

It has been found that, surprisingly, water contents within a range of more than 15 to 25% by weight, preferably 18 to 22% by weight, based on the total amount used, and when a hydrogenation temperature of 110 to 180° C., preferably of 110 to 140° C., is established, it is possible to selectively hydrogenate hydroxypivalaldehyde to neopentyl glycol, and the very selective cleavage of high boilers which form during the reaction of isobutyraldehyde with formaldehyde to give neopentyl glycol is possible. The high boilers are oxygen-containing compounds, such as esters or cyclic acetals, in which equivalents of neopentyl glycol are chemically bound. In the high boilers, the proportion of mono- and diisobutyric esters of neopentyl glycol and of the disproportionation product neopentyl glycol monohydroxypivalate formed by the Tishchenko reaction from hydroxypivalaldehyde is particularly high. The inventive adjustment of the hydrogenation step in relation to the water content in the starting material and the exact selection of the hydrogenation temperature allow high boilers already present in the starting material to be cleaved effectively to neopentyl glycol and the formation thereof during the hydrogenation reaction to be suppressed, compared to a mode of operation in which a starting material with a water content of less than 15% by weight is used or a hydrogenation temperature of less than 110° C. is employed.

When the water contents in the starting material are too low, no advantageous effect is observed any longer on the reduction of the high boiler content, and, when the hydrogenation temperatures are too low, hydroxypivalaldehyde is hydrogenated only incompletely. At excessively high water contents, valuable reactor volume is occupied unnecessarily and not exploited. At excessively high hydrogenation temperatures, decomposition of the tertiary alkylamine used as the aldolization catalyst likewise occurs, which leads to conversion products which are difficult to remove and is therefore undesired.

The aldol addition of isobutyraldehyde and of an aqueous formaldehyde solution is effected in the presence of tertiary alkylamines as an aldol addition catalyst, for example, in the presence of trimethylamine, triethylamine, tri-n-propylamine, triisopropylamine, methyldiethylamine, methyldiisopropylamine or tributylamine. Particularly suitable catalysts have been found to be triethylamine and tri-n-propylamine.

The aldehydes can be reacted in a molar ratio, but it is also possible to employ one of the two reactants in excess. Formaldehyde is used as an aqueous solution; the aldehyde content is typically from 20 to 50% by weight. The reaction is effected at temperatures between 20 and 100° C.; it is appropriate to work at 80 to 95° C. In general, the reaction is performed at standard pressure, but it is also possible to employ elevated pressure. The tertiary alkylamine used as the aldol addition catalyst is present in the reaction mixture in an amount of 1 to 20 and preferably 2 to 12 mol %, based on isobutyraldehyde.

In addition to the water from the aqueous formaldehyde solution and small proportions of methanol which is likewise present in the aqueous formaldehyde solution, isobutanol is optionally also added to the reaction mixture as a diluent. Isobutanol addition is not absolutely necessary; if, however, isobutanol is added, its content in the reaction mixture is in the range from 10 to 20% by weight based on the entire reaction mixture. Further solvents and diluents are not required.

In practical terms, the addition reaction is performed in a stirred tank or in a reaction tube which is equipped with random packings for better mixing of the reactants. The reaction proceeds exothermically; it can be accelerated by heating.

The crude mixture obtained after the aldol addition is catalytically hydrogenated without preceding separation into its constituents or removal of individual components. What is essential for the inventive hydrogenation of the hydroxypivalaldehyde-containing reaction mixture is compliance with a defined water content, a defined hydrogenation temperature and a particular reaction pressure. When the amount of water introduced through the use of the aqueous formaldehyde solution is insufficient to ensure the required water content, water should be added to the crude product before use in the hydrogenation reactor.

The hydrogenation is likewise effected in the presence of an aliphatic alcohol which is miscible with the crude aldolization product. Suitable aliphatic alcohols have been found to be linear or branched alcohols having 1 to 5 carbon atoms, for example, methanol, ethanol, n-propanol, isopropanol, n-butanol, isobutanol or mixtures thereof. It is particularly appropriate to use isobutanol, since residual amounts of isobutyraldehyde are hydrogenated to isobutanol. If isobutanol is already used as a diluent in the aldol addition stage, a solvent is already present in the hydrogenation stage. Small amounts of methanol which are introduced via the aqueous formaldehyde solution are likewise present. The proportion of the aliphatic alcohol as an organic solvent or diluent is 15 to 27% by weight, preferably 15 to 18% by weight, based on the organic component in the starting mixture. The addition of the diluent or solvent ensures sufficient solubility of the hydroxypivalaldehyde in the liquid phase during the hydrogenation stage, and also prevents the precipitation of hydroxypivalaldehyde and ensures the homogeneity of the liquid phase.

The entire starting mixture used for the hydrogenation is homogeneous and thus contains more than 15 and up to 25% by weight of water and, as the remainder to 100% by weight, an organic component which in turn contains 15 to 27% by weight of an aliphatic alcohol.

The resulting hydroxypivalaldehyde-containing crude mixture is hydrogenated without further workup and purification steps.

The hydrogenation of the crude hydroxypivalaldehyde is performed at a temperature of 110 to 180° C., preferably of 110 to 140° C., in the liquid phase in the presence of nickel catalysts. The reaction pressure is 6 to 18 MPa, preferably 8 to 15 MPa. At lower reaction pressures, satisfactory hydrogenation of the hydroxypivalaldehyde is no longer observed.

Nickel as the catalytically active metal can be applied to a support, generally in an amount of about 5 to 70% by weight, preferably about 10 to about 65% by weight and especially about 20 to 60% by weight, based in each case on the total weight of the catalyst. Suitable catalyst supports are all conventional support materials, for example, aluminum oxide, aluminum oxide hydrates in their various manifestations, silicon dioxide, polysilicic acid (silica gels) including kieselguhr, silica xerogel, magnesium oxide, zinc oxide, zirconium oxide and activated carbon. In addition to the main nickel and support material components, the catalysts may also contain additives in minor amounts, which, for example, serve to improve their hydrogenation activity and/or their service life and/or their selectivity. Such additives are known; examples include the oxides of sodium, of potassium, of magnesium, of calcium, of barium, of zinc, of aluminum, of zirconium, and of chromium. They are added to the catalyst generally in a total proportion of 0.1 to 50 parts by weight, based on 100 parts by weight of nickel.

However, it is also possible to use Raney nickel as a support-free catalyst.

The hydrogenation is performed continuously in the liquid phase, for example over fixed bed catalysts by the trickle mode or liquid phase mode.

In continuous mode, a catalyst hourly space velocity V/Vh expressed in throughput volume per unit catalyst volume and time, of 0.3 to 2.0 $h^{-1}$, preferably 0.8 to 1.2 $h^{-1}$, has been found to be appropriate.

A higher space velocity on the nickel catalyst should be avoided because the hydroxypivalaldehyde starting compound is then no longer completely hydrogenated and increased by-product formation is observed.

The hydrogenation is performed continuously in the liquid phase in a tubular reactor over fixed bed catalysts. A tubular reactor is also understood to mean a bundle of a plurality of tubes connected closely in parallel. The hydrogenation of hydroxypivalaldehyde is effected in a tubular reactor without internals and without stirrer apparatus.

The hydrogenation is effected preferably with pure hydrogen. However, it is also possible to use mixtures which comprise free hydrogen and additionally constituents which are inert under the hydrogenation conditions.

The pure neopentyl glycol is obtained from the hydrogenated reaction mixture by conventional distillation processes. Solvent or diluent removed can be recycled back into the aldol addition stage and/or hydrogenation stage.

In the hydrogenation process according to the invention, hydroxy-pivalaldehyde is converted to neopentyl glycol at high conversion with high selectivity. What is remarkable is the low proportion of high boilers after hydrogenation.

The hydrogenation process according to the invention very selectively hydrogenates the hydroxypivalaldehyde starting compound with high conversion to neopentyl glycol, and the high boilers formed in the preceding aldol addition stage are effectively cleaved and their formation in the hydrogenation stage is suppressed in a lasting manner. The cleavage of the tertiary alkylamine to volatile nitrogen-containing compounds which lead to undesired impurities and which can be removed only with difficulty in the subsequent distillative workup and which are disruptive in the further processing of neopentyl glycol is also suppressed.

The process according to the invention is illustrated in detail hereinafter with reference to some examples, but it is not restricted to the embodiments described.

Test Setup

The liquid phase hydrogenation was effected over a commercial supported nickel catalyst in the tubular reactor in liquid phase mode. The catalyst volume was 1.8 liters. The hydroxypivalaldehyde-containing crude aldol addition product and hydrogen were supplied continuously at the bottom of the tubular reactor. The hydrogenated material was withdrawn via the top of the tubular reactor, passed into a high-pressure separator and conducted out of the latter by means of level control into an ambient pressure reservoir. The hydrogenation temperature, the hydrogen pressure and the catalyst hourly space velocity were adjusted according to the conditions of the tables which follow. The crude hydroxypivalaldehyde-containing aldol addition product used for the hydrogenation tests had the following typical composition.

Organic component (determined by gas chromatography, data in percent):

| | |
|---|---|
| Low boilers | 0.1 |
| Isobutanol | 2.0 |
| Methanol | 0.9 |
| Intermediate runnings | 7.5 |
| Isobutanol | 21.1 |
| HPA | 62.3 |
| NPG | 2.2 |
| TE | 2.9 |
| Final runnings | 1.0 |
| Water | 18.5% by weight based on the overall starting mixture |

HPA = hydroxypivalaldehyde
NPG = neopentyl glycol
TE = Tishchenko ester/NPG diisobutyrate In the analysis data given below for the starting streams, the critical contents for the aliphatic alcohols serving as diluents and the water content were reported. In the analysis of the hydrogenation outputs, the residual contents of HPA and of ester compounds and the NPG content were stated.

Liquid phase hydrogenation of HPA at a hydrogenation temperature of 130° C.

TABLE 1

Pressure 8 MPa

| Test | V/Vh [$h^{-1}$] | Analysis of the starting streams, determined by gas chromatography, in percent*) | | Water**) % by weight | Analysis of the hydrogenation effluents, determined by gas chromatography, in percent | | | | |
|---|---|---|---|---|---|---|---|---|---|
| | | Isobutanol | Methanol | | HPA | TE | NPG | Low boilers | High boilers |
| 1 | 0.27 | 19.6 | 1.0 | 18.9 | 0.1 | 6.2 | 67.1 | 25.0 | 1.6 |
| 2 | 0.53 | 21.0 | 0.9 | 15.7 | 0.1 | 5.2 | 65.0 | 28.2 | 1.5 |
| 3 | 0.90 | 23.9 | 1.2 | 15.2 | 1.0 | 3.9 | 62.8 | 31.1 | 1.2 |

TABLE 2

Pressure 6 MPa

| Test | V/Vh [h$^{-1}$] | Analysis of the starting streams, determined by gas chromatography, in percent*) | | Water**) % by weight | Analysis of the hydrogenation effluents, determined by gas chromatography, in percent | | | | |
|---|---|---|---|---|---|---|---|---|---|
| | | Isobutanol | Methanol | | HPA | TE | NPG | Low boilers | High boilers |
| 4 | 1.00 | 22.9 | 1.0 | 18.4 | 0.4 | 4.0 | 62.9 | 31.3 | 1.4 |
| 5 (comparative) | 0.90 | 23.3 | 0.9 | 14.6 | 0.1 | 4.4 | 61.8 | 32.2 | 1.5 |

TABLE 3

Pressure 14 MPa

| Test | V/Vh [h$^{-1}$] | Analysis of the starting streams, determined by gas chromatography, in percent*) | | Water**) % by weight | Analysis of the hydrogenation effluents, determined by gas chromatography, in percent | | | | |
|---|---|---|---|---|---|---|---|---|---|
| | | Isobutanol | Methanol | | HPA | TE | NPG | Low boilers | High boilers |
| 6 | 1.00 | 22.9 | 1.0 | 16.1 | 0.2 | 3.7 | 63.3 | 31.2 | 1.6 |
| 7 | 1.33 | 22.1 | 1.1 | 18.5 | 0.4 | 2.5 | 65.0 | 30.7 | 1.4 |
| 8 (comparative) | 1.50 | 22.7 | 1.1 | 14.4 | 1.6 | 3.1 | 62.0 | 31.5 | 1.8 |

TABLE 4

Pressure 4 MPa

| Test | V/Vh [h$^{-1}$] | Analysis of the starting streams, determined by gas chromatography, in percent*) | | Water**) % by weight | Analysis of the hydrogenation effluents, determined by gas chromatography, in percent | | | | |
|---|---|---|---|---|---|---|---|---|---|
| | | Isobutanol | Methanol | | HPA | TE | NPG | Low boilers | High boilers |
| 9 (comparative) | 0.90 | 23.6 | 1.6 | 16.9 | 4.7 | 4.5 | 55.7 | 33.3 | 1.8 |

*)based on the organic component in the overall starting mixture
**)water in % by weight, based on the overall starting mixture As a comparison of the test data shows, the proportion of the desired NPG in the hydrogenation output also increases with rising water content in the starting mixture. When, for example, proceeding from test 3, the water content is established below the critical limit of 15% by weight (comparative test 5), the NPG content in the hydrogenation output is lowered. This development is also manifested in tests 6, 7, and 8 (comparative), in which the content of NPG in the hydrogenation output likewise decreases with falling water content in the starting material. The pressure selected in comparative example 9 is no longer sufficient for a satisfactory HPA conversion.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention which is set forth in the claims of this case.

The invention claimed is:

1. A continuous process for preparing neopentyl glycol, comprising the steps of:
   a.) producing hydroxypivalaldehyde by addition of isobutyraldehyde and formaldehyde in the presence of a tertiary alkylamine as a catalyst;
   b.) passing a starting mixture comprising:
      (i.) hydroxypivalaldehyde produced in step a.);
      (ii.) an aliphatic alcohol in an amount of 15 to 27% by weight of the organic component in the starting mixture;
      (iii.) hydrogen; and
      (iv.) water in an amount of more than 15 to 25% by weight, based on the total mass of the starting mixture;
   to a tubular reactor without internals and without stirrer apparatus and
   c.) hydrogenating said hydroxypivalaldehyde at a temperature of 110 to 180° C.; and a pressure of 6 to 18 MPa in the presence of a catalyst chosen from the group consisting of:

(i.) nickel dispersed on a solid support;
(ii.) nickel and an oxide of: sodium; potassium; magnesium; calcium; barium; zinc; aluminum; zirconium; chromium or a combination of any of these oxides; and
(iii.) Raney nickel.

2. The process of claim 1, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

3. The process of claim 1, wherein the tertiary alkylamine used is chosen from the group consisting of triethylamine and tri-n-propylamine.

4. The process of claim 3, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

5. The process of claim 1, wherein the starting mixture comprises water in an amount of 18 to 22% by weight based on the total mass of the starting mixture.

6. The process of claim 5, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

7. The process of claim 5, wherein the tertiary alkylamine is chosen from the group consisting of triethylamine and tri-n-propylamine.

8. The process of claim 7, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

9. The process of claim 1, wherein the hydrogenation is performed at a temperature of 110 to 140° C. and at a pressure of 8 to 15 MPa.

10. The process of claim 9, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

11. The process of claim 9, wherein the tertiary alkylamine is chosen from the group consisting of triethylamine and tri-n-propylamine.

12. The process of claim 9, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

13. The process of claim 9, wherein the starting mixture comprises water in an amount of 18 to 22% by weight based on the total mass of the starting mixture.

14. The process of claim 13, wherein the aliphatic alcohol is chosen from the group consisting of: linear or branched alcohols having 1 to 5 carbon atoms; methanol, ethanol, n-propanol, isopropanol, n-butanol, isobutanol or mixtures thereof.

15. The process of claim 14, wherein the tertiary alkylamine is chosen from the group consisting of triethylamine and tri-n-propylamine.

16. The process of claim 1, wherein said starting mixture comprising: hydroxypivalaldehyde; an aliphatic alcohol; hydrogen; and water is in the form of a homogeneous liquid when brought into contact with said catalyst.

17. The process of claim 1, wherein said starting mixture comprising: hydroxypivalaldehyde; an aliphatic alcohol; hydrogen; and water is passed to said tubular reactor from step a.) substantially without separation into its individual constituents or removal of individual constituents.

18. The process of claim 1, wherein said tubular reactor is filled with random packings.

19. The process of claim 1, wherein:
(i.) the aliphatic alcohol comprises isobutanol,
(ii.) said starting mixture comprising: hydroxypivalaldehyde; an aliphatic alcohol; hydrogen; and water is in the form of a homogeneous liquid when brought into contact with said catalyst and is passed to said tubular reactor from step a.) substantially without separation into its individual constituents or removal of individual constituents; and
(iii.) said tubular reactor is filled with random packings.

20. The process of claim 19, wherein the starting mixture comprises water in an amount of 18 to 22% by weight based on the total mass of the starting mixture and the hydrogenation is performed at a temperature of 110 to 140° C. and at a pressure of 8 to 15 MPa.

* * * * *